United States Patent [19]
Kahn

[11] 3,949,476
[45] Apr. 13, 1976

[54] DEVICE USEFUL IN DENTAL CROWN PROCEDURES AND METHOD OF USING THE SAME

[76] Inventor: Henry Kahn, 366 Dell, Highland Park, Ill. 60035

[22] Filed: Mar. 25, 1974

[21] Appl. No.: 454,154

[52] U.S. Cl. .................................... 32/12; 32/17
[51] Int. Cl.² .................................... A61C 5/08
[58] Field of Search .......... 32/17, 12, 13, 15, 40 R, 32/41, 60, 70

[56] References Cited
UNITED STATES PATENTS

| | | |
|---|---|---|
| 3,004,343 | 10/1961 | Rydin ........................................ 32/13 |
| 3,521,357 | 7/1970 | Berglund et al. ........................ 32/71 |
| 3,748,741 | 7/1973 | Yerkes, Jr. ................................ 32/71 |

*Primary Examiner*—Louis G. Mancene
*Assistant Examiner*—Jack Q. Lever

[57] ABSTRACT

A device and method useful in the restoration of an abraded or broken tooth by the application to the stub, of a crown to replace the abraded or broken portions, the crown being secured to a prepared core. There is disclosed a "direct" method of preparing the core for the crown and a device to facilitate fabrication of the core and installation of the same in the mouth comprising simple, time-saving steps.

18 Claims, 16 Drawing Figures

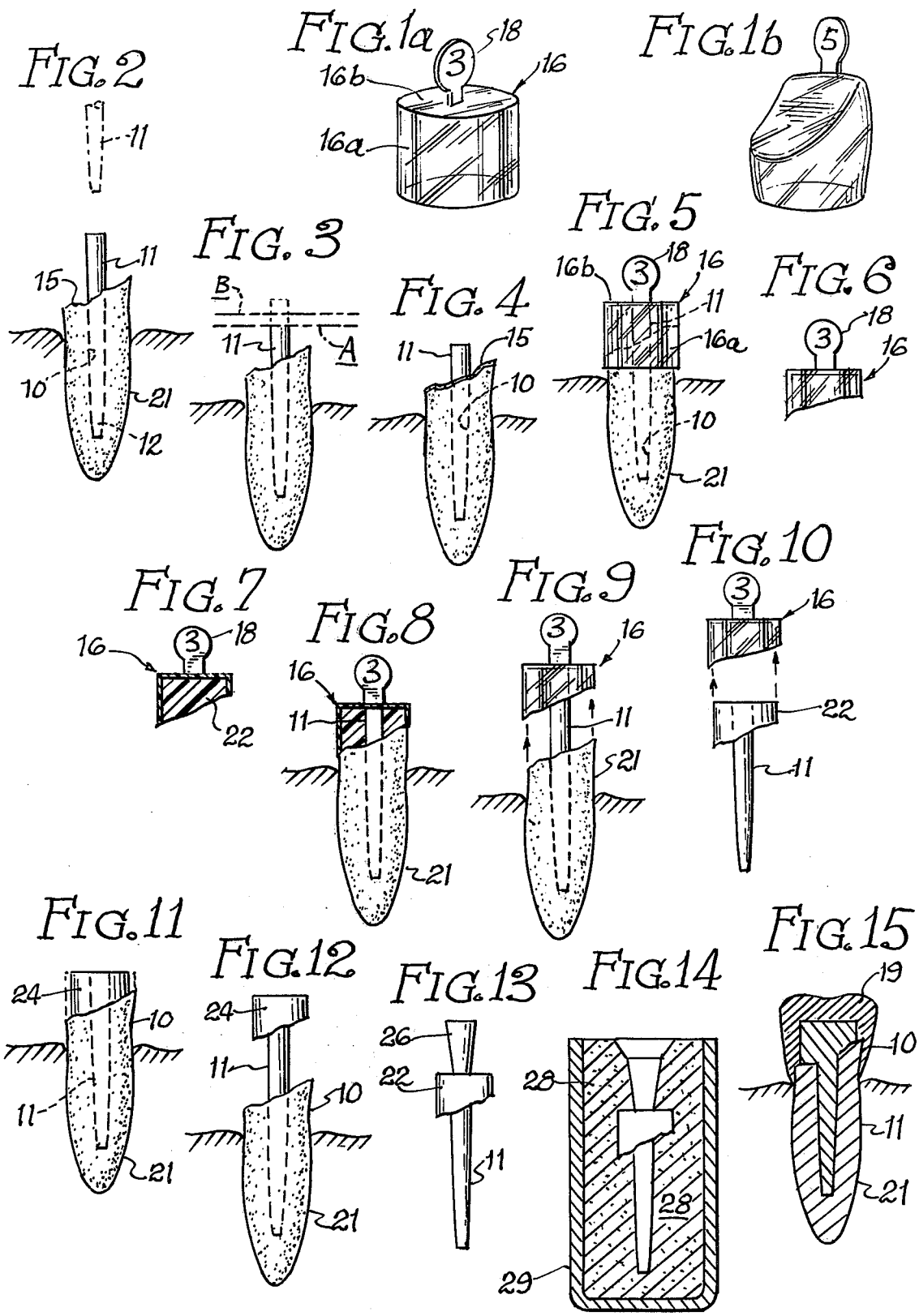

DEVICE USEFUL IN DENTAL CROWN PROCEDURES AND METHOD OF USING THE SAME

BACKGROUND OF THE INVENTION

Where, herein, I employ the words "direct method" I refer to a procedure wherein the major portion of the work is performed within the patient's mouth and by the words "indirect method" I refer to a procedure wherein the major portion of the work is done outside the mouth.

The invention relates to restoration of a mutilated tooth, e.g. one which has been abraded or broken, by fitting a crown thereto. Although the principles of the invention are disclosed with reference to a gold crown, it finds equal utility with crowns of other metallic media as well as those of porcelain and other non-metallic media.

Cases requiring endodontia (root canal therapy) are, in nearly every case, coronally weak to begin with. During the root canal treatment, they are further weakened by the need to gain adequate access to the canal or canals. In turn, this requires reinforcement of the remainder of the tooth before placement of the crown. This is usually done by the use of a post fitting within the canal and a hard core integrated with the post to receive the crown. The post usually occupies the upper two-thirds of the canal and the core is usually located in the pulp chamber as well as in a portion of the stub of the tooth. This core need be built only high enough to mount and reinforce the final crown. The post and core assembly is usually of gold and is cemented in place.

One direct method, heretofore known, is referred to as the "Adaptic" technique and uses a metal post cemented into the canal, pins screwed into the stub and a core built up on the post and pins by employing a plastic composition, e.g. that known as Adaptic. This composition is a restorative material available from Johnson & Johnson, 20 Lake Drive, East Windsor, N.J. 08520. Adaptic is the trademark under which the product is sold. The mentioned post and pins are secured in the stub and the pins are provided with enlargements or hooks at the outer end adapted to interlock with a mass of air-hardenable plastic retained in position against the stub by means of a "crown form" pending hardening. However, following hardening and removal of the crown form the operator must grind off a large volume of plastic to produce a core of the desired size and shape. This last is, in general, the method pursued when preparing a tooth for a porcelain or gold crown. However, the patient is discommoded and inordinate time consumed.

One method somewhat favored for front teeth is to fill a transparent crown form with a plastic moldable material, position it over the post which has been previously secured in the canal and allow the material to set.

In one indirect method, a metal or plastic post is located in a die and the core is built up outside the mouth with wax, drop by drop, to the approximate size and is then shaped with an instrument. The post and core is separated from the die and the casting is made by the lost-wax technique.

Another indirect method entails a rubber impression of the stub of the tooth including the hole in the canal and a die or model is then made from this impression. Then the post (metallic or plastic) is located in the model and the wax core portion is made on it. Casting is by the classical lost wax process. Should the dentist desire to vary this method by indirect steps, considerable time will be saved since, instead of building up the core (in this case, wax) drop by drop, he can still use a core form as he would in the mouth.

In any of the indirect techniques, fabrication of the core outside of the mouth is extremely time-consuming and, hence, uncomfortable for the patient.

When using wax for the core portion one can employ either a post of metal, e.g. gold, or plastic but neither is cemented in the root canal. On the contrary the post is removed after the wax core has been built thereon in order that the casting may be made in a crucible. This casting will include a replica of the post which is then cemented into the tooth. When using a metal post, the wax is replaced by the poured metal. When using a plastic post, the core portion, together with the post portion, are cast in one piece.

SUMMARY OF THE INVENTION

The present invention has for its principal objects the provision of a form and a method of utilizing the same whereby formation of the core portion may be performed in the mouth in much less time than has hitherto been the case. The form is preferably of transparent plastic that will be made commercially available to the dentist in a range of sizes calculated to fit closely around the stub, depending upon its size. The form is provided with a handle to render placement and removal thereof somewhat easier. The handle or body of the device preferably bears an identifying number or letter to simplify its selection from a kit of the several sizes. By the use of a form of this kind the direct method is considerably simplified, irrespective of the material employed for the post or core.

BRIEF DESCRIPTION OF THE DRAWING

FIG. 1a is a perspective view of one embodiment of the form of the invention;

FIG. 1b is an elevational view of another embodiment; and

FIGS. 2 to 15 illustrate steps in carrying out the method of the invention.

DESCRIPTION OF THE PREFERRED EMBODIMENT

Assuming that the necessary work on the root canal 10 of the stub 21 of the tooth has been completed, a dowel or post 11 is inserted in the canal with a snug fit (FIG. 2). At this juncture it will be understood that where reference is made to the "canal", the term is intended to encompass plural canals and that the dowel or post will be used within at least one thereof. Optionally, a lubricant may be used to facilitate subsequent withdrawal of the post. The post is selected overlength and, therefore, is trimmed on a plane A just below the estimated position of the occlusal plane B of the tooth (FIG. 3). At this stage the patient will close his jaws so that the position of the top surface of the post can be verified and, if necessary, the post shortened or a longer post substituted. The irregular surface 15 of the tooth is then coated with any suitable separating medium, e.g. mineral oil (FIG. 4).

It is to be noted that the exemplificative case herein described assumes restoration of a lower tooth. Obviously, in the case of an upper tooth, everything will be reversed.

The device 16 employed in carrying out the invention method takes two basic configurations shown in FIGS. 1a and 1b and is in the shape of a cup having a cylindrical or substantially cylindrical lateral wall 16a and an end wall 16b. It will be fabricated of a transparent, thin, but relatively rigid plastic composition having a good memory. The configuration of FIG. 1a may be termed the posterior type and that of FIG. 1b, the anterior type. To facilitate handling, a knob 18 is provided and, since the device 16 will, desirably, be supplied to the practitioner in a kit containing various sizes to accommodate the smallest, as well as the largest teeth these several sizes can be suitably identified, as by numerals or letters, as indicated in the figure.

Now, a device 16 of the proper size, is located over the stub 21 (FIG. 5) and a line noted upon which the lateral wall 16a is to be festooned to conform to the irregular surface of the stub 21. While marking the device for festooning, the same is held high enough to allow for later formation of the core. It is possible to permit the end wall 16b of the device to rest on the post 11. It will be understood that the thickness of the side wall 16a will be such as to respond readily to shearing. After being festooned (FIG. 6) the device is inverted and filled with wax, self-curing plastic, e.g. a dipolymer, acrylic resin or other medium which is readily worked when set (FIG. 7).

The form and its charge of wax or other medium still in the soft, but not runny stage, is then forced over the stub (FIG. 8). The excess will be squeezed out at the lower margin of the side wall 16a and immediately trimmed away.

As soon as the core 22 is hard the device 16, together with the core and post 11 embedded therein, are removed from the mouth (FIG. 9) and the device 16 is cut and stripped from the core 22 (FIG. 10). Alternatively, while the core is still in place on the tooth, the device 16 can be slit with a sharp instrument and stripped separately. The core and post are re-assembled with the stub (FIG. 11) and the flanks and occlusal surface are shaped in conformance with the surfaces of the original tooth but allowing for the ultimate crown to be fitted into place. The thus-shaped core 22 and post 11 are separated from the stub 21 as an assembly and removed from the mouth (FIG. 12).

A sprue 26 of incinerable material, e.g. plastic composition, is added to the core 22 in any preferred position (FIG. 13).

The assembly of FIG. 13 can now be used as the pattern for the investment material 28 carried in the crucible 29 (FIG. 14). The ultimate casting is then made by the usual lost wax process, and is fitted and attached to the stub 21 in accordance with established practice, whereafter the crown 19 is fabricated and secured.

I claim:

1. A form for the preparation of the core for a crown in the restoration of a broken or otherwise degraded tooth wherein said core is to be secured to at least one post in the stub of the tooth, said form being cup shaped with an end wall which lies at least parallel to the normal occlusal plane of the tooth, a continuous side wall extending from the periphery of the end wall, the cup having transverse interior dimensions to define a space to accommodate the stub and surrounding the same, the space being adapted to receive a core casting material to be placed around the post, the edge of said side wall opposite said end wall being shaped to conform to the irregular surface of said stub, at least said side wall comprising a readily machinable, relatively rigid material, the form further having a handle protruding from said end wall.

2. A core form useful in the restoration of a broken or otherwise degraded anterior tooth by mounting a crown on a core secured to the stub of the tooth, said form being cup-shaped comprising a side wall conforming substantially to a truncated cylindrical surface encircling the tooth, and an end wall conforming to the plane of truncation, said side and end walls defining a space adapted to accommodate the stub and surrounding the same, the space being adapted to receive a casting material around the post and stub, at least said side wall comprising a readily machinable, relatively rigid material and a handle protruding from said end wall.

3. A device in accordance with claim 1 wherein the material is a plastic.

4. A device in accordance with claim 2 wherein the material is a plastic.

5. The device in accordance with claim 4 in which the plastic is a resin.

6. The device in accordance with claim 5 wherein the resin is thermoplastic.

7. The device in accordance with claim 5 wherein the resin is an acrylic.

8. The device in accordance with claim 3 in which the plastic is polyethylene.

9. The device in accordance with claim 4 in which the plastic is polyethylene.

10. The device in accordance with claim 3 in which the plastic is a vinyl.

11. The device in accordance with claim 4 in which the plastic is a vinyl.

12. The method of fabricating a core for the mounting of a crown on the remaining stub of a degraded tooth which comprises the steps of:
  a. preparing the root canal to receive a post;
  b. inserting the post in the canal;
  c. cutting the post to length;
  d. providing a readily machinable, substantially cylindrical cup having a lateral wall and an end wall;
  e. locating the cup over the stub to determine a festooning line;
  f. removing the cup from the mouth;
  g. festooning the lateral wall on the determined line;
  h. filling the festooned cup with a pasty, hardenable composition;
  i. placing the thus-filled cup in its former location and concurrently embedding the post in the composition;
  j. removing the squeezed-out excess composition;
  k. allowing the composition to harden to form a core pattern;
  l. removing the cup with the composition therein and the post seized therein from the mouth;
  m. separating the cup from the core pattern;
  n. re-locating the core with the post in its previous position;
  o. trimming the core to correspond with the original tooth portion;
  p. removing the shaped core and its post from the mouth;
  q. attaching a sprue to the core pattern;
  r. preparing a mold from the core pattern and sprue;
  s. casting the core pattern and sprue in the mold;
  t. separating the casting from the mold; and u. separating the sprue from the core.

13. The method of fabricating a core for the mounting of a crown on the remaining stub of a degraded tooth which comprises the steps of:
   a. inserting a post of selected length in the root canal;
   b. providing a readily machinable, substantially cylindrical cup having a lateral wall and an end wall;
   c. locating the cup over the stub to determine a festooning line;
   d. removing the cup from the mouth;
   e. festooning the cup;
   f. filling the festooned cup with a pasty, hardenable composition;
   g. placing the thus-filled cup in its former location and concurrently embedding the post in the composition;
   h. allowing the composition to harden to form a core pattern;
   i. removing the core pattern comprising the cup and composition and the post seized therein from the mouth;
   j. separating the cup from the core pattern;
   k. casting the core by the lost wax technique; and
   l. removing the casting from the mold.

14. The method in accordance with claim 13 further characterized by the additional step, following step (j) of replacing the core pattern in the mouth and trimming the same to correspond with the original tooth portion.

15. The method in accordance with claim 13 further characterized by the additional step, following step (j) of adding a sprue to the core pattern.

16. The method in accordance with claim 7 further characterized by the additional step, following step (l) of removing the sprue from the casting.

17. The method in accordance with claim 13 further characterized in that the lateral wall of the cup of step (b) has an interior configuration conforming substantially to the lateral wall of the stub.

18. The method of fabricating a core for the mounting of a crown on the remaining stub of a degraded tooth which comprises the steps of:
   a. inserting a post of selected length in the root canal;
   b. providing a readily machinable, substantially cylindrical cup having a lateral wall and an end wall;
   c. locating the cup over the stub to determine a festooning line;
   d. removing the cup from the mouth;
   e. festooning the cup;
   f. filling the festooned cup with a pasty, hardenable composition;
   g. placing the thus-filled cup in its former location and concurrently embedding the post in the composition;
   h. allowing the composition to harden to form a core pattern;
   i. removing the core pattern comprising the cup and composition and the post seized therein from the mouth.

* * * * *

UNITED STATES PATENT OFFICE
CERTIFICATE OF CORRECTION

Patent No. 3,949,476           Dated April 13, 1976

Inventor(s) Henry Kahn

It is certified that error appears in the above-identified patent and that said Letters Patent are hereby corrected as shown below:

Column 4, lines 5 to 17 should read as follows:

2. A core form useful in the restoration of a broken or otherwise degraded anterior tooth by mounting a crown on a core secured to the stub of the tooth, said form being cup-shaped comprising a side wall conforming substantially to a truncated cylindrical surface encircling the tooth, and an end wall conforming to the plane of truncation, said side and end walls defining a space adapted to accommodate the stub and surrounding the same, the space being adapted to receive a casting material around the post and stub, at least said side wall comprising a readialy machinable, relatively rigid material and a handle protruding from said end wall.

Signed and Sealed this

[SEAL]

Twenty-eighth Day of September 1976

*Attest:*

RUTH C. MASON
*Attesting Officer*

C. MARSHALL DANN
*Commissioner of Patents and Trademarks*

UNITED STATES PATENT AND TRADEMARK OFFICE
CERTIFICATE OF CORRECTION

PATENT NO. : 3,949,476
DATED : April 13, 1976
INVENTOR(S) : Henry KAHN

It is certified that error appears in the above-identified patent and that said Letters Patent are hereby corrected as shown below:

Column 4, lines 5 to 17 should read as follows:

-- 2. A form for the preparation of the core for a crown in the restoration of a broken or otherwise degraded anterior tooth wherein said core is to be secured to at least one post in the stub of the tooth, said form being cup-shaped comprising a side wall having one edge conforming substantially to a truncated cylindrical surface encircling the stub, and an end wall for said one edge conforming to the plane of truncation, the opposite edge of said side wall conforming to the irregular surface of said stub, said side and end walls defining a space adapted to accommodate the stub and surrounding the same, the space being adapted to receive a core casting material to be placed around the post, at least said side wall comprising a readily machinable, relatively rigid material and a handle protruding from said end wall. --

This certificate supersede Certificate of Correction issued September 28, 1976.

Signed and Sealed this

Seventh Day of June 1977

[SEAL]

Attest:

RUTH C. MASON
Attesting Officer

C. MARSHALL DANN
Commissioner of Patents and Trademarks